(12) United States Patent
McSpadden

(10) Patent No.: US 7,731,498 B2
(45) Date of Patent: Jun. 8, 2010

(54) ENDODODONTIC FILE WITH MULTI-TAPERED FLUTES

(76) Inventor: John T. McSpadden, 1403 Patten Rd., Lookout Mountain, GA (US) 30750

( * ) Notice: Subject to any disclaimer, the term of this patent is extended or adjusted under 35 U.S.C. 154(b) by 672 days.

(21) Appl. No.: 11/373,015

(22) Filed: Mar. 10, 2006

(65) Prior Publication Data

US 2006/0228668 A1    Oct. 12, 2006

Related U.S. Application Data

(63) Continuation-in-part of application No. 10/440,040, filed on May 16, 2003, now abandoned.

(60) Provisional application No. 60/660,793, filed on Mar. 11, 2005.

(51) Int. Cl.
*A61C 5/02* (2006.01)

(52) U.S. Cl. .................................................. 433/102

(58) Field of Classification Search ................. 433/102, 433/165, 224
See application file for complete search history.

(56) References Cited

U.S. PATENT DOCUMENTS

| | | | |
|---|---|---|---|
| 251,598 A | 12/1881 | Johanson | |
| 4,260,379 A | 4/1981 | Groves et al. | |
| 4,353,698 A * | 10/1982 | McSpadden | 433/164 |
| 4,824,370 A | 4/1989 | Laurichesse et al. | |
| 4,871,312 A * | 10/1989 | Heath | 433/102 |
| 5,035,617 A | 7/1991 | McSpadden | |
| 5,236,357 A | 8/1993 | Randin | |
| 5,464,362 A | 11/1995 | Heath et al. | |
| 5,692,902 A * | 12/1997 | Aeby | 433/102 |
| 5,735,689 A * | 4/1998 | McSpadden | 433/102 |
| 5,842,862 A | 12/1998 | Nissan | |
| 5,897,316 A * | 4/1999 | Buchanan | 433/102 |
| 6,074,209 A | 6/2000 | Johnson | |
| 6,206,695 B1 | 3/2001 | Wong et al. | |
| 6,267,592 B1 | 7/2001 | Mays | |
| 6,299,445 B1 | 10/2001 | Garman | |
| 6,419,488 B1 | 7/2002 | McSpadden et al. | |
| 6,428,317 B1 | 8/2002 | Abel | |
| 6,702,579 B1 * | 3/2004 | Hoppe et al. | 433/102 |
| 7,125,252 B2 * | 10/2006 | Rouiller et al. | 433/102 |
| 2005/0272004 A1* | 12/2005 | Desrosiers | 433/102 |

FOREIGN PATENT DOCUMENTS

| | | |
|---|---|---|
| EP | 0120542 | 10/1984 |
| WO | WO 02/065938 A1 | 8/2002 |

* cited by examiner

*Primary Examiner*—Cris L Rodriguez
*Assistant Examiner*—Heidi M Eide
(74) *Attorney, Agent, or Firm*—Luedeka, Neely & Graham, P.C.

(57) ABSTRACT

A multi-tapered endodontic file is provided, formed from shaft of material having a shaft. The shaft includes a working portion having one or more tissue-removing edges, points and/or surfaces. The working portion includes at least a first flute and a second flute. The first flute is tapered along its length in accordance with a first predetermined taper function. The second flute is tapered along its length in accordance with a second predetermined taper function.

3 Claims, 6 Drawing Sheets

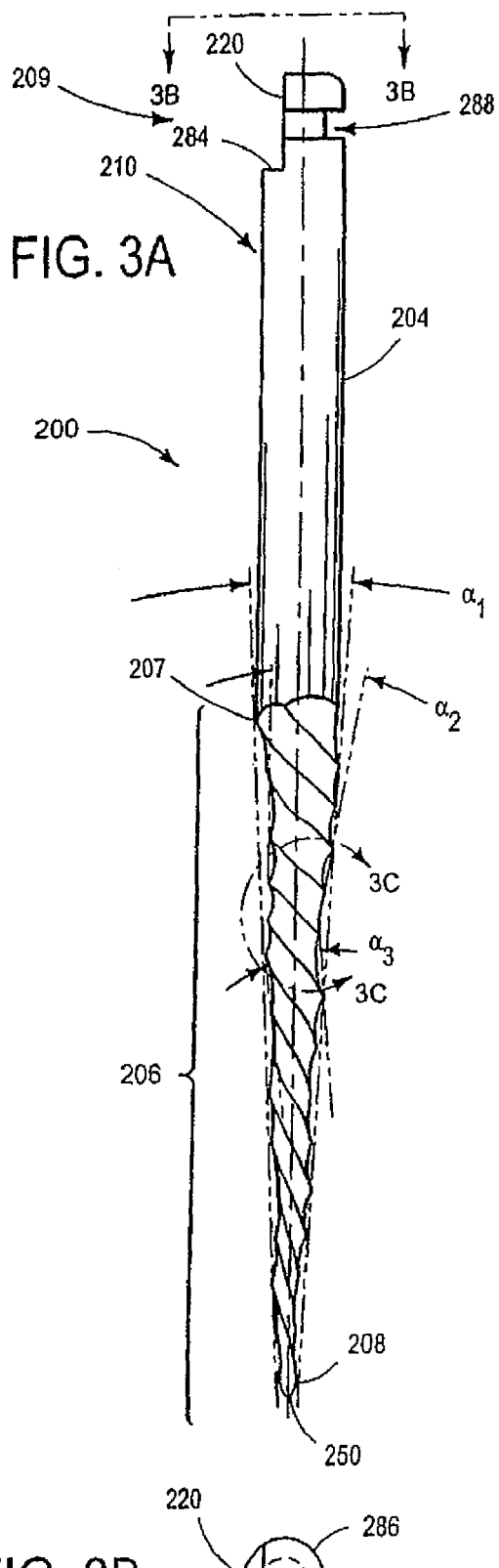
FIG. 3A
FIG. 3B
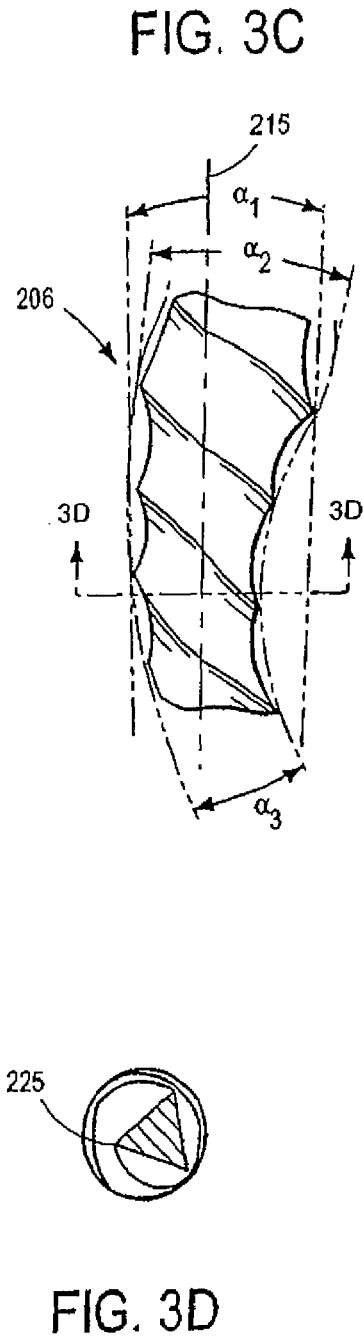
FIG. 3C
FIG. 3D

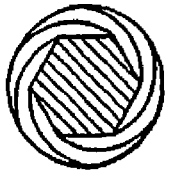
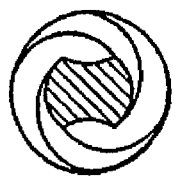
FIG. 4A            FIG. 4B            FIG. 4C
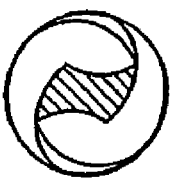
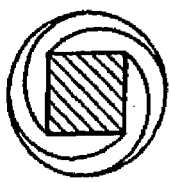
FIG. 4D            FIG. 4E            FIG. 4F
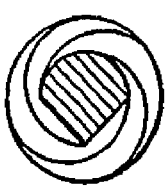
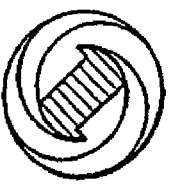
FIG. 4G            FIG. 4H            FIG. 4I
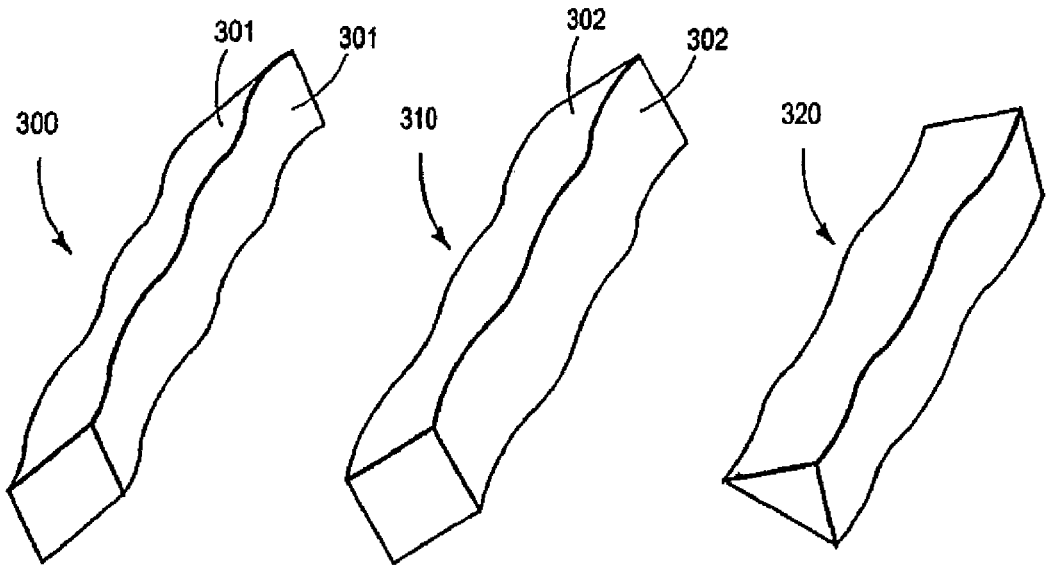
FIG. 5A            FIG. 5B            FIG. 5C

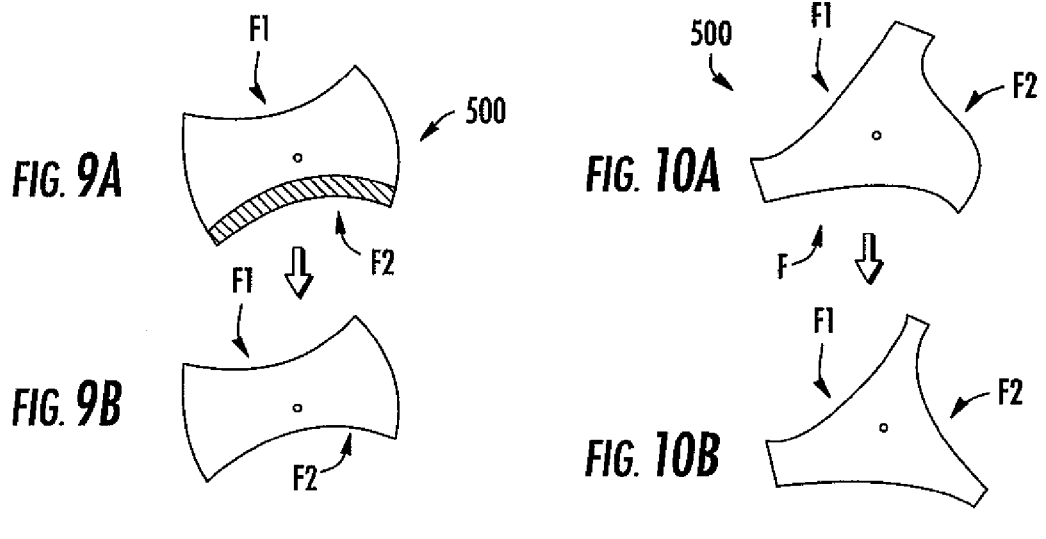
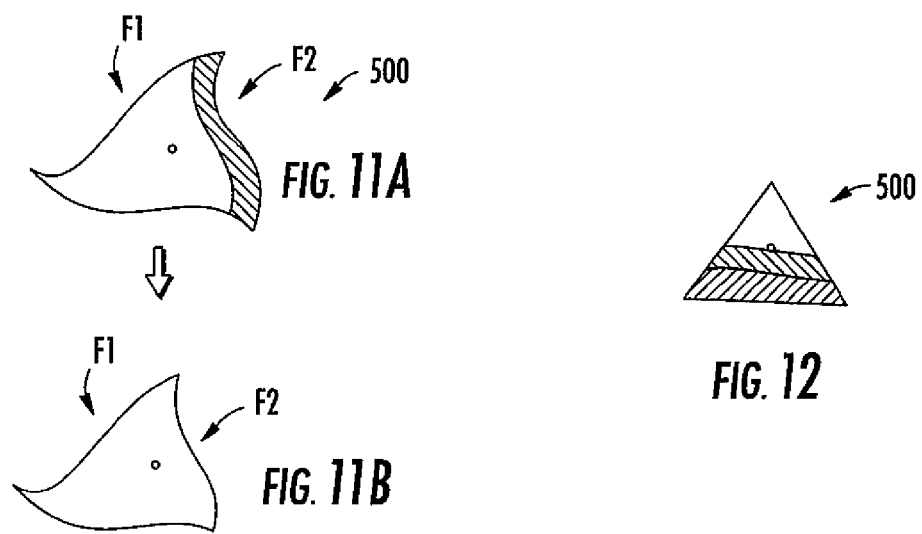

ENDODODONTIC FILE WITH MULTI-TAPERED FLUTES

CROSS REFERENCE TO RELATED APPLICATIONS

This application claims priority under 35 U.S.C. §119(e) to provisional application Ser. No. 60/660,793 filed Mar. 11, 2005 and is a continuation-in-part of U.S. patent application Ser. No. 10/440,040, filed May 16, 2003 now abandoned.

FIELD OF THE INVENTION

The present invention relates generally to the field of dentistry and more particularly to an endodontic instrument for cleaning and enlarging a root canal.

BACKGROUND OF THE INVENTION

In the field of endodontics, one of the most important and delicate procedures is that of cleaning or extirpating a root canal to provide a properly dimensioned cavity while essentially maintaining the central axis of the canal. This step is important in order to enable complete filling of the canal without any voids and in a manner which prevents the entrapment of noxious tissue in the canal as the canal is being filled.

In a root canal procedure, the dentist removes inflamed tissue and debris from the canal prior to filling the canal with an inert filling material. In performing this procedure the dentist must gain access to the entire canal, shaping it as necessary. But root canals normally are very small in diameter, and they can often be quite curved. It is therefore very difficult to gain access to the full length of a root canal.

Many tools have been designed to perform the difficult task of cleaning and shaping root canals. Historically, dentists have used a wide multitude of tools to remove the soft and hard tissues of the root canal. These tools, usually called endodontic files, have been made by three basic processes. In one process, a file is created by twisting a prismatic rod of either square or triangular cross section in order to create a file with helical cutting/abrading edges ("K-file"). The second process involves grinding helical flutes into a circular or tapered rod to create a file with one or more helical cutting edges ("Hedstrom file"). The third method involves "hacking" or rapidly striking a circular or tapered rod with a blade at a given angle along the length of the rod, thus creating an endodontic file characterized by a plurality of burr-like barbs or cutting edge projections ("barbed file" or "broach"). Each of these instruments and manufacturing processes has unique advantages, and disadvantages.

A particularly problematic aspect of current state-of-the-art endodontic files, particularly K-files and Hedstrom files, is catastrophic failure caused by torque overload. Often, files will become lodged or jammed within the canal such that continued twisting or turning can cause the file to fail or break off in the canal. For endodontic files having twisting or helically spiraling cutting edges, such files can often unexpectedly engage or borough into the root canal, inadvertently driving the instrument deep into the root canal and possibly puncturing the apical seal thereof and/or otherwise transporting through the canal wall (so-called "screwing-in effect"). Another prevalent problem is heavy torque loading caused by inefficient cutting and/or high surface area engagement of the file with the inner canal wall. Excessive torque loading is problematic because it increases the friction heat generated within the canal per file revolution, increasing the chance of bone necrosis and/or catastrophic failure of the file/reamer instrument.

Accordingly, there is a need for an improved endodontic file design which overcomes these and other problems

SUMMARY OF THE INVENTION

It is therefore an object of the present invention to provide an improved endodontic file design having reduced torque loading and reduced tendency to screw in to the canal. It is another object of the invention to provide an endodontic instrument having a reduced tendency to break during use. It is another object of the invention to improve the efficacy of an endodontic instrument and/or to reduce the number of instruments necessary to enlarge a root canal. It is another object of the invention to provide a technique for increasing or reducing the flexibility and/or blade engagement of an endodontic instrument in order to enhance extirpating and obturating procedures.

According to one embodiment of the present invention, a multi-tapered endodontic instrument is provided. The instrument comprises an elongated shaft having a working portion having one or more tissue-removing edges, points and/or surfaces defined thereon. The instrument also includes and a plurality of flutes comprising at least a first flute and a second flute. The first flute has a taper with respect to a longitudinal axis of the working portion that is defined by a first taper function and the second flute having a taper with respect to the longitudinal axis of the working portion that is defined by a second taper function. The first taper function is different than the second taper function.

For purposes of summarizing the invention and the advantages achieved over the prior art, certain objects and advantages of the invention have been described herein above. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which:

FIG. 3A is a side elevation view of an alternative embodiment of a multi-tapered endodontic instrument;

FIG. 3B is a top plan view of the fitting portion of the multi-tapered endodontic instrument of FIG. 3A;

FIG. 3C is a detail view of the working portion of the multi-tapered endodontic instrument of FIG. 3A having a first generally helical taper enveloped within a second substantially linear outer taper;

FIG. 3D is a partial cross-section view of the working portion of the multi-tapered endodontic instrument of FIG. 3A;

FIGS. 4A-I are partial transverse cross-section views of additional alternative embodiments of a multi-tapered endodontic instrument;

FIGS. 5A-C are perspective views of multi-tapered rods suitable for forming multi-tapered K-files;

FIGS. 6A-12 are cross-sectional views of modified embodiments of an endodontic file having certain features and advantages according the present invention.

DETAILED DESCRIPTION OF THE PREFERRED EMBODIMENT

Figure 1:
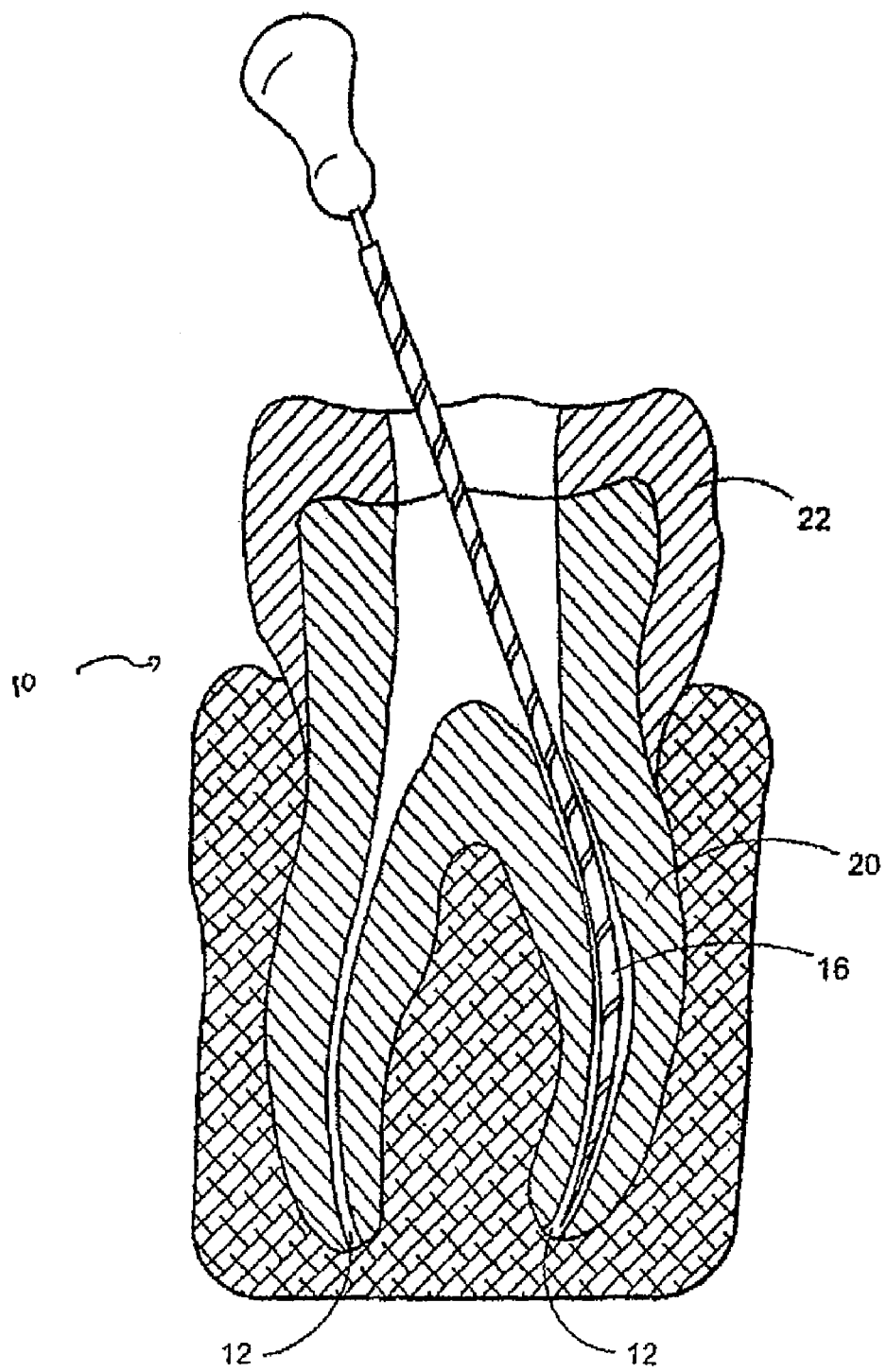
FIG. 1 is a section view of a tooth and root structure illustrating the use of a typical endodontic instrument for performing a typical root canal procedure.

FIG. 1 is a partial cross section of a tooth 10 and supporting root structure illustrating the use of a typical fluted endodontic file 16 to carry out a standard root canal procedure. The root canal 12 of a tooth houses the circulatory and neural systems of the tooth. These enter the tooth at the terminus of each of its roots 20 and extend through a narrow, tapered canal system to a pulp chamber adjacent a crown portion 22 of the tooth 10. If the pulp tissue within the canal 12 becomes diseased or injured, it can cause severe pain and trauma to the tooth, sometimes necessitating extraction of the tooth. Root canal therapy involves removing the diseased tissue from the canal 12 and sealing the canal system in its entirety. If successful, root canal therapy can effectively alleviate the pain and trauma associated with the tooth so that it need not be extracted.

To perform a root canal procedure, the endodontist first drills into the tooth 10 to locate the root canal(s) 12 and then uses an endodontic file or reamer instrument 16 to remove the decayed, injured or dead tissue from the canal 12. These instruments are typically elongated cutting or abrading instruments which are rotated and/or reciprocated within the root canal either by hand or using a slow speed drill. The primary goal is to remove all of the decayed or injured nerve while leaving the integrity of the root canal walls relatively unaffected. Preserving the integrity of the root canal 12 is important in order to allow proper filling of the root canal void in a homogenous three dimensional manner such that leakage or communication between the root canal system and the surrounding and supporting tissues of the tooth 10 is prevented. Once as much of the diseased material as practicable is removed from the root canal 12, the canal system is sealed closed, typically by reciprocating and/or rotating a condenser instrument in the canal to urge a sealing material such as gutta-percha into the canal.

One of the primary challenges in performing root canal therapy is that the root canals are not necessarily straight and are often curved or convoluted. Therefore, it is often difficult to clean the canal while preserving its natural shape. Many instruments (particularly the older, stainless steel instruments) have a tendency to straighten out the canal or to proceed straight into the root canal wall, altering the natural shape of the canal. In some extreme cases, the instrument may transport completely through the canal wall causing additional trauma to the tooth and/or surrounding tissues. Also, the openings of many root canals are small, particularly in older patients, due to calcified deposits on the root canal inner walls. Thus the files or reamers must be able to withstand the torsional load necessary to penetrate and enlarge the canal opening without breaking the instrument, as may also occasionally occur with the older stainless steel endodontic files.

To alleviate the transportation and breakage problems, highly flexible endodontic files fabricated from nickel-titanium alloy (Nitinol™ or NiTi) were introduced and have become widely accepted. See, e.g. U.S. Pat. No. 5,882,198, incorporated herein by reference. A series of comparative tests of endodontic instruments made of nickel-titanium alloy (Nitinol™ or NiTi) and stainless steel were conducted and published in an article entitled "An Initial Investigation of the Bending and the Torsional Properties of Nitinol Root Canal Files," Journal of Endodontics, Volume 14, No. 7, July 1988, pages 346-351. The reported tests demonstrated that the NiTi instruments exhibited superior flexibility and torsional properties as compared to stainless steel instruments.

In general, alloys of nickel (Ni) and titanium (Ti) have a relatively low modulus of elasticity (0.83 GPa) over a wide range, a relatively high yield strength (0.195-690 MPa), and the unique and the unusual property of being "superelastic" over a limited temperature range. Superelasticity refers to the highly exaggerated elasticity, or spring-back, observed in many NiTi and other superelastic alloys over a limited temperature range. Such alloys can deliver over 15 times the elastic motion of a spring steel, i.e., withstand twisting or bending up to 15 times greater without permanent deformation. The particular physical and other properties of Nitinol alloys may be varied over a wide range by adjusting the precise Ni/Ti ratio used.

Conventional fluted instruments 16 (even those fabricated of NiTi) also suffer from an occasional tendency to bind and/or to advance unpredictably into the root canal 12 by virtue of a "screwing-in" effect as the instrument is rotated. In many cases, this binding or screwing-in effect can result in the file breaking inside the canal. In the most severe cases, the fluted instrument 16 can actually drive itself through the terminus of the canal 12 and into the patient's jaw bone and surrounding soft tissues.

FIGS. 2A-D illustrate an exemplary embodiment of a multi-tapered endodontic file 100. The file 100 generally comprises a shaft 110 having a shank portion 104 and an elongated working portion 106. The working portion 106 extends from a proximal end 107 adjacent the base of the shank 104 to a distal end 108 terminating in a tip 150. The shank portion 104 preferably includes a fitting portion 109 for mating with the chuck of a dental handpiece (not shown). The fitting portion 109 includes a generally I-shaped flat side 120 which defines a step 184 and a generally semicircular disk 186 above and adjacent to a generally semi-circular groove 188. Such a fitting 109 is typical of those employed in the dental industry for connecting or interfacing a dental tool with dental drill or handpiece. Of course, in other embodiments, the fitting 109 may be modified for connecting or interfacing with non-typical or other types of dental tools.

Alternatively and/or in addition to the fitting portion 109, the shank portion 104 may include a knurled or otherwise treated surface (not shown) or handle to facilitate hand manipulation of the file 100 (see, e.g., FIG. 1). Thus, the instrument 100 may either be used by manipulating the instrument manually in a rotating or reciprocating action, or the instrument may be manipulated by attaching the fitting portion 109 of the instrument to a motorized handpiece for effecting more rapid removal of tissue from the root canal, as desired.

The working portion 106 of the instrument 100 preferably has a length ranging from about 3 mm to about 18 mm. A preferred length is about 16 mm. The outer envelope of the working portion 106 is preferably shaped in accordance with a first taper function from the proximal end 107 to the distal end 108, as shown. In the particular embodiment shown, the first taper function is an elongated cone having a substantially uniform angle of conicity $\alpha_1$ that is, the rate of taper or cone angle is substantially constant along the working portion 106. A preferred first taper function ranges from a constant taper rate about 0.01 mm/mm to about 0.08 mm/mm. Alternatively, the first taper function may vary over the length of the working portion 106 or follow any other regular or irregular/random function, as desired.

The outer envelope of the working portion 106 is further defined in accordance with a second taper function—different from the first—that preferably varies from a positive taper angle ($\alpha_2$) to negative taper angle ($\alpha_3$) along at least a portion of the length of the working portion 106. In the particular embodiment illustrated the second taper function is defined by a generally sinusoidal function having either constant or varying frequency and/or amplitude. More preferably, the second taper function follows a periodic or repeating function, such as a sine function, cosine function or the like. Most preferably, the second taper function follows an underdamped second-order sinusoidal decay function having the following characteristic equation:

$$f(x)=[Ae^{(-\alpha \cdot \chi)} \cdot \sin(\beta \cdot \chi + \phi)]$$

where:
$Ae^{(-\alpha \cdot \chi)}$=damped amplitude (outer diameter)
$\beta/2\pi$=quasi-frequency
$\phi$=phase angle One or more cutting edges 125 are preferably formed along the working portion 108 of the instrument 100. These may be formed, for example, by twisting an appropriately shaped multi-tapered prismatic rod (see, e.g., FIGS. 5A-C) and/or by forming helical flutes in a tapered or multi-tapered blank via suitable grinding operations. The cutting edges may have a negative, positive or neutral rake angle, as desired. Alternatively, one or more barbs, notches, abrasive surfaces and/or the like may be used in addition to or instead of cutting edges 125 to provide the desired tissue removal capability of the instrument 100. The tip 150 of the instrument 100 may assume any number of a variety of possible configurations (e.g., chisel, cone, bullet, multi-faceted and/or the like), depending upon the preference of the endodontist and manufacturing conveniences. Again, those skilled in the art will readily appreciate that the particular geometries can be varied without departing from the essential teachings disclosed herein.

Those skilled in the art will appreciate that the particular pattern of exposed cutting edges or other cutting/abrading surfaces can be suitably controlled or modulated by combining multiple taper functions to achieve optimal performance for each particular application. In the particular example illustrated, the size of the cross-section of the working portion 106 alternatingly expands and contracts from the proximal end 107 to the distal end 108 within an envelope defined by the first and second taper functions while remaining essentially concentric with the central axis 115 of the instruments 100.

Advantageously, the multi-tapered endodontic file 100 according to the illustrate embodiment described above is highly efficacious in cleaning and expanding root canal openings. Multi-tapering causes the particular shape, distribution and/or orientation of cutting edges 125 to be arranged and exposed in such a way as to increase cutting efficiency, reduce friction and torque loading on the instrument 100. In particular, it is believed that multi-tapering decreases the percentage of cutting surfaces in contact with the root canal wall at any given time, thereby increasing localized cutting forces or bearing pressures of each engaged cutting edge portion while simultaneously reducing overall torque loading of the instrument. This increases cutting efficiency of the engaged cutting edge portions. Multi-tapering of the instrument working portion 106 in this manner also increases the flexibility of the instrument in bending without sacrificing overall strength or resistance to torque. This greatly improves the performance of the instrument in curved root canals for a given material and cross-section, allowing larger diameter files to be used in highly curved root canals. In turn, this improves the speed and efficacy of the root canal procedure and reduces the number of endodontic files and other specialized tools required to complete each procedure. Because multi-tapering reduces simultaneous engagement of the instrument cutting edges 125, multi-tapered instruments also have less tendency to "screw in" to the root canal. This adverse tendency can be further reduced by combining additional taper functions that act specifically to counteract the forward advancing forces produced by helical cutting edges (see, e.g., FIGS. 3A-D and the accompanying disclosure).

The shank 110 is preferably (but not necessarily) formed from a rod of nickel titanium alloy, such as SE508 nickel-titanium wire manufactured by Nitinol Devices and Components, Inc. of Fremont, Calif. This is a typical binary nickel-titanium alloy used for endodontic files and comprises about 56% nickel and about 44% titanium by weight. Table 1, below, summarizes certain selected material properties of the SE508 NiTi alloy:

TABLE 1

SE508 MATERIAL PROPERTIES PHYSICAL PROPERTIES

| PHYSICAL PROPERTIES | |
|---|---|
| Melting Pont | 1310° C. |
| Density | 6.5 g/cm$^3$ |
| Electrical Resistivity | 82 µohm-cm |
| Modulus of Elasticity | 75 × 10$^6$ MPa |
| Coefficient of Thermal Expansion | 11 × 10$^{-6}$/° C. |
| MECHANICAL PROPERTIES | |
| Ultimate Tensile Strength (UTS) | 1150 MPa |
| Total Elongation | 10% |
| SUPERELASTIC PROPERTIES | |
| Loading Plateau Stress @ 3% strain | 450 MPa |
| Superelastic Strain (max) | 8% |
| Permanent Set (after 6% strain) | 0.2% |
| Transformation Temperature (AF) | 5–18° C. |
| COMPOSITION | |
| Nickel (nominal) | 55.8 wt. % |
| Titanium (nominal) | 44.2 wt. % |
| Oxygen (max) | 0.05 wt. % (max) |
| Carbon (max) | 0.02 wt. % (max) |

If desired, special heat treatments may be employed and/or trace elements of oxygen (O), nitrogen (N), iron (Fe), aluminum (Al), chromium (Cr), cobalt (Co) vanadium (V), zirconium (Zr) and/or copper (Cu), may be added to achieve desired mechanical properties. See, for example, U.S. Pat. No. 5,843,244 to Pelton, incorporated herein by reference.

While nickel-titanium alloys are preferred, the invention disclosed herein is not limited as such, but may be practiced using a wide variety of other suitable alloys, including other super-elastic alloys and conventional medical-grade stainless steel and/or nickel alloys.

Figure 2A:
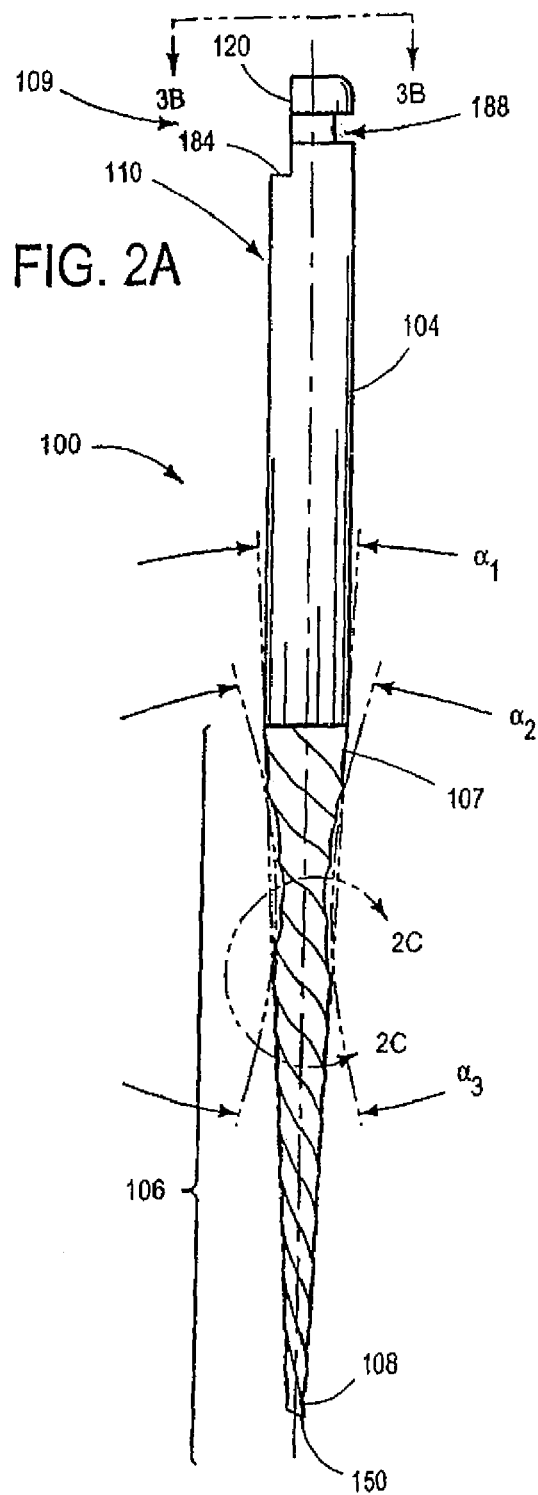
FIG. 2A is a side elevation view of a multi-tapered endodontic instrument.
Figure 2C:
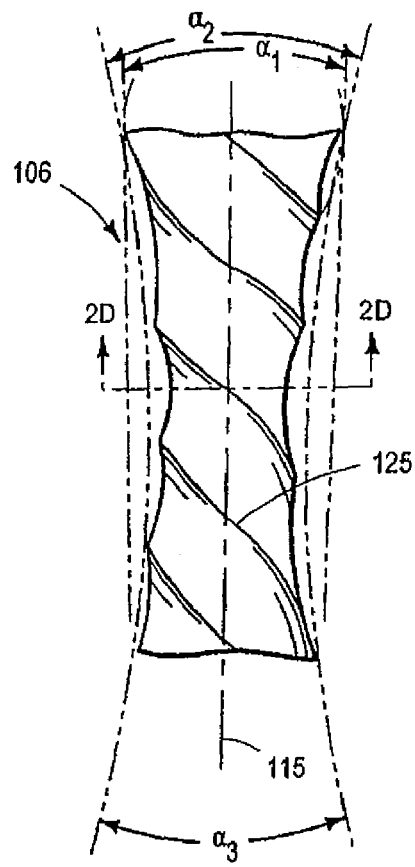
FIG. 2C is a detail view of the working portion of the multi-tapered endodontic instrument of FIG. 2A having a first generally sinusoidal taper enveloped within a second substantially linear outer taper.
Figure 2B:
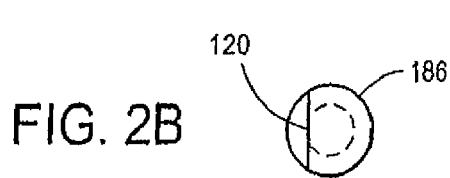
FIG. 2B is a top plan view of the fitting portion of the multi-tapered endodontic instrument of FIG. 2A.
Figure 2D:
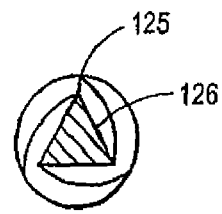
FIG. 2D is a partial cross-section view of the working portion of the multi-tapered endodontic instrument of FIG. 2A.

In one embodiment, the shaft 110 is rolled, ground, extruded or otherwise machined to produce an elongated prismatic structure having a desired multi-tapered geometric shape in cross-section (see, e.g., FIGS. 5A-C). A triangular cross-section is particularly preferred, having three flat facing surfaces ("flats") 126 and three corners 125 (preferably sharp), as illustrated in FIG. 2D. Of course, those skilled in the art will readily appreciate that a wide variety of other shapes may also be used with efficacy, such as triangular, hexagonal, octagonal, rectangular, or other regular polygon. Certain irregular polygons may also be used with efficacy such as those formed with one or more exposed corners and one or more facing surfaces (flat or otherwise).

FIGS. 4A-4I illustrate various modified embodiments of cross-section shapes that may be used with efficacy. In each of the examples illustrated, it should be understood that the helix angle or angle of twist of the instrument can run either clockwise or counterclockwise (or both) as desired. While a symmetrical sinusoidal decay taper function is illustrated, those skilled in the art will appreciate that a wide variety of multiple taper functions may be used with efficacy, such as linear or non-linear functions, symmetric or asymmetric sine functions, saw-tooth functions, regular or irregular/random functions, and/or the like.

FIGS. 3A-D illustrate a modified exemplar embodiment of a multi-tapered endodontic file. As with the embodiment of FIGS. 2A-2D, the file 200 generally comprises a shaft 210 having a shank portion 204 and an elongated working portion 206. The working portion 206 extends from a proximal end 207 adjacent the base of the shank 204 to a distal end 208 terminating in a tip 250. The shank portion 204 preferably includes a fitting portion 209 for mating with the chuck of a dental handpiece (not shown). The fitting portion 209 includes a generally I-shaped flat side 220 which defines a step 284 and a generally semicircular disk 286 above and adjacent to a generally semi-circular groove 288. Such a fitting 209 is typical of those employed in the dental industry for connecting or interfacing a dental tool with dental drill or handpiece. Of course, in modified embodiments, the fitting 209 may be modified to fit with non-typical or different types of dental tools.

As described above, alternatively and/or in addition to the fitting portion 209, the shank portion 204 may include a knurled or otherwise treated surface (not shown) or handle to facilitate hand manipulation of the file 200 (see, e.g., FIG. 1). Thus, the instrument 200 may either be used by manipulating the instrument manually in a rotating or reciprocating action, or the instrument may be manipulated by attaching the fitting portion 209 of the instrument to a motorized handpiece for effecting more rapid removal of tissue from the root canal, as desired.

The working portion 206 of the instrument 200 preferably has a length ranging from about 3 mm to about 18 mm. A preferred length is about 16 mm. The outer envelope of the working portion 206 is preferably shaped in accordance with a first taper function from the proximal end 207 to the distal end 208, as shown. In the particular embodiment shown, the first taper function is an elongated cone having a substantially uniform angle of conicity $\alpha_1$—that is, the rate of taper or cone angle is substantially constant along the working portion 206. A preferred first taper function ranges from a constant taper rate about 0.01 mm/mm to about 0.08 mm/mm. Alternatively, the first taper function may vary over the length of the working portion 206 or may follow any other regular or irregular/random function, as desired.

The outer envelope of the working portion 206 is further defined in accordance with a second taper function—different from the first—that preferably retains a positive taper angle along at least a portion of the length of the working portion 206 from taper angle ($\alpha_2$) to negative taper angle ($\alpha_3$), but which effectively modulates the center axis of the cross-section relative to the central axis 215 of the instrument 200.

In the particular embodiment illustrated, the second taper function is defined by a generally sinusoidal function having either constant or varying frequency and/or amplitude. More preferably, the second taper function follows a periodic or repeating function, such as a sine function, cosine function or the like. Most preferably, the second taper function follows an underdamped second-order sinusoidal decay function having the following characteristic equation:

$$f(x) = [Ae^{(-\alpha \cdot \chi) - 1.2} \cdot \sin(\beta \cdot \chi + \phi)]$$

where:

$Ae^{(-\alpha \cdot \chi)}$ = damped amplitude (outer diameter)
$\beta/2\pi$ = quasi-frequency
$\phi$ = phase angle One or more cutting edges 225 are preferably formed along the working portion 206 of the instrument 200. These may be formed, for example, by twisting an appropriately shaped multi-tapered prismatic rod (see, e.g., FIGS. 5A-C) and/or by forming helical flutes in a tapered or multi-tapered blank via suitable grinding operations. The cutting edges may have a negative, positive or neutral rake angle, as desired. Alternatively, one or more barbs, notches, abrasive surfaces and/or the like may be provided in addition to or instead of cutting edges 225 to provide a desired amount of tissue removal capability of the instrument 200. The tip 250 of the instrument 200 may assume any number of a variety of possible configurations (e.g., chisel, cone, bullet, multi-faceted and/or the like), depending upon the preference of the endodontist and manufacturing conveniences. Again, those skilled in the art will readily appreciate that the particular geometries can be varied without departing from the teachings disclosed herein.

Those skilled in the art will appreciate that the particular pattern of exposed cutting edges or other cutting/abrading surfaces can be suitably controlled or modulated by combining multiple taper functions to achieve optimal performance for each particular application. In the particular example illustrated, the cross-section of the working portion 206 tapers substantially continuously while simultaneously winding cork-screw-like from the proximal end 207 to the distal end 208 within an envelope defined by the first and second taper functions.

Advantageously, the multi-tapering of the instrument in accordance with the above-embodiments causes the particular shape, distribution and/or orientation of cutting edges 225 to be arranged and exposed in such a way as to increase cutting efficiency, reduce friction and torque loading on the instrument 200. In particular, it is believed that multi-tapering decreases the percentage of cutting surfaces in contact with the root canal wall at any given time, thereby increasing localized cutting forces or bearing pressures of each engaged cutting edge portion while simultaneously reducing overall torque loading of the instrument. This increases cutting efficiency of the engaged cutting edge portions. Multi-tapering of the instrument working portion 206 in this manner also increases the flexibility of the instrument in bending without sacrificing overall strength or resistance to torque. This greatly improves the performance of the instrument in curved root canals for a given material and cross-section.

Because multi-tapering reduces simultaneous engagement of the instrument cutting edges 225, multi-tapered instruments also have less tendency to "screw in" to the root canal. This adverse tendency is further reduced by selecting one or more taper functions that act specifically to counteract the forward advancing forces produced by helical cutting edges. For example, the multi-tapered instrument 200 illustrated in FIGS. 3A-D preferably includes a reverse helical taper function (reverse cork-screw shape) that tends to counteract the forward advancing forces created by the helical cutting edges 225. Thus, if the tip of the instrument 200 were to suddenly bind in the canal, the reverse helical taper would effectively help urge the file out of the canal. Thus, the overall safety of the root canal procedure is greatly improved.

In accordance with one preferred manufacturing technique any variety of multi-tapered instruments may be fabricated by twisting a suitably formed multi-tapered rod such as illustrated in FIGS. 5A-C. For example, FIG. 5A illustrates a tapered rod 300 having a generally square cross section that tapers in and out repeatedly along the length of the rod. A sinusoidal taper function having a determined amplitude and wave length is applied to each face 301 of the rod 300. On adjacent faces 301 the sinusoidal taper functions are in phase. On opposite faces 301 the sinusoidal taper functions are 180.degree. out of phase. In this manner, the cross-section of the rod remains substantially square and essentially concentric throughout its length, but varies in size in accordance with the sinusoidal taper function. Those skilled in the art will readily appreciate that the particular phase, frequency and/or amplitude of each taper function can also be varied or adjusted independently of the other taper functions so as to create various desired interference patterns between the multiple taper functions FIG. 5B illustrates a tapered rod 310 having a generally square cross section that tapers back and forth repeatedly along the length of the rod. A sinusoidal taper function having a determined amplitude and wave length is applied to each face 302 of the rod 310. On adjacent faces 302 the sinusoidal taper functions are 180.degree. out of phase. On opposite faces 302 the sinusoidal taper functions are in phase. In this manner, the cross-section of the rod remains substantially square and of the same size throughout its length, but moves back and forth and left to right in a cork-screw fashion relative to the centerline of the rod in accordance with the sinusoidal taper function. Those skilled in the art will readily appreciate that the particular phase, frequency and/or amplitude of each taper function can also be varied or adjusted independently of the other taper functions so as to create various desired interference patterns between the multiple taper functions.

FIG. 5C illustrates a tapered rod 320 having generally the same taper functions as the rod 310 in FIG. 5B, except having a generally triangular cross section with three flats and preferably three sharp corners, as illustrated. Those skilled in the art will readily appreciate that a wide variety of alternative taper functions and cross-sections having various constant or non-constant phase angles, wave lengths and frequencies may be used and combined together to produce any variety of desired performance characteristics. Useful taper functions may include, without limitation, straight linear taper functions, horn-shaped or flared taper functions, exponential or lognormal taper functions, repeating and/or non-repeating taper functions, sinusoidal taper functions, saw-tooth taper functions, random taper functions, and the like.

Alternatively, or in addition, any variety of multi-tapered instruments may be fabricated by grinding operations using a 3-axis or, more preferably, a 6-axis computer-controlled grinding machine programmed with a suitable instruction set. In this manner, any variety of complex instrument designs having multiple superimposed taper functions may be programmed and useful instruments may be readily fabricated therefrom. Each tapering and/or fluting operation may be performed as a separate manufacturing step, or, alternatively, multiple tapers and/or fluting may be formed simultaneously. Grinding operations are particular preferred for producing multi-tapered instruments with sharp, positive- or neutral-rake-angle cutting edges. Grinding operations are also particularly preferred for refining and testing commercial prototypes since various multiple-taper designs can be readily programmed, manufactured and tested with relative ease. Those skilled in the art will readily appreciate that various multi-tapered file designs can also be tested, adjusted and optimized according to specific tasks, functions, root canal types and/or user-preferences.

FIGS. 6A-12 are cross-sectional shapes of a modified embodiment of an endodontic file 500 with multi-tapered flutes as described below.

As with the previous embodiments, the file 500 generally comprises a shaft having a shank portion and an elongated working portion. As will be explained in more detail below, FIGS. 6A-12 illustrate cross-sections along the working portion for various different embodiments of the file 500. In these embodiments, the working portion extends from a proximal end adjacent the base of the shank to a distal end terminating in a tip. The shank portion preferably includes a fitting portion for mating with the chuck of a dental handpiece. The fitting portion may include a generally I-shaped flat side which defines a step and a generally semicircular disk above and adjacent to a generally semi-circular groove. Such a fitting is typical of those employed in the dental industry for connecting or interfacing a dental tool with dental drill or handpiece. Of course, in other embodiments, the fitting may be modified for connecting or interfacing with non-typical or other types of dental tools.

Alternatively and/or in addition to the fitting portion, the shank portion may include a knurled or otherwise treated surface or handle to facilitate hand manipulation of the file 500 (see, e.g., FIG. 1). Thus, the file may either be used by manipulating the instrument manually in a rotating or reciprocating action, or the instrument may be manipulated by attaching the fitting portion of the instrument to a motorized handpiece for effecting more rapid removal of tissue from the root canal, as desired.

The working portion of the file 500 preferably has a length ranging from about 3 mm to about 18 mm. A preferred length is about 16 mm. As with the previous embodiments, the outer envelope of the working portion is preferably shaped in accordance with a first taper function from the proximal end to the distal end. In one embodiment, the first taper function defines an elongated cone having a substantially uniform angle of conicity $\alpha_1$. That is, the rate of taper or cone angle is substantially constant along the working portion. A preferred first taper function ranges from a constant taper rate about 0.01 mm/mm to about 0.08 mm/mm. Alternatively, the first taper function may vary over the length of the working portion 106 or follow any other regular or irregular/random function, as desired. In still another embodiment, the first taper function may be constant or substantially constant through all or a majority of the working portion. In such an embodiment, the tip portion may be tapered or rounded.

As shown in FIGS. 6A-12, in the present embodiment, the file 500 preferably includes two or more flutes (F), which are formed into the working portion. In certain embodiments, the flutes may be formed in a helical pattern into a circular or tapered rod using any of the techniques described above to create a file with one or more helical cutting edges. In other embodiments, the flutes need not be formed in a helical pattern. In prior art files with helical flutes, each of the flutes has the same taper from the central axis of the instrument. That is, all of the flutes are tapered in accordance with the same taper function This arrangement results in proportional changes in the flute dimensions in an axial direction along the working portion.

In contrast, in the illustrated embodiments, the endodontic file 500 has at least one flute F1 (i.e., a "first flute") that tapers in accordance with a first taper function $f_1$. The first taper function may be constant (e.g., having a constant positive taper angle $\alpha_2$) or it may vary (e.g., from a positive taper angle ($\alpha_2$) to negative taper angle ($\alpha_3$) in a manner as defined above). Another flute F2 (i.e., a "second flute") tapers in accordance with a second taper function $f_2$, which is different than the first taper function $f_1$. For example, in one embodiment, the first flute F1 tapers along a first positive taper angle and the second flute F2 tapers along a second positive taper angle that may be larger or smaller than the first positive taper angle. In another embodiment, the first flute's taper varies along its path according to a first taper function $f_1$ and the second flute's taper varies along its path according to a second taper function $f_2$, which is different than the first taper function $f_1$ In a similar manner, additional flutes may be provide that may taper according to the first and second taper functions ($f_1, f_2$) or a different taper function ($f_n$).

In one embodiment, the difference between the first taper function $f_1$ and the second taper function $f_2$. results in changes in the flute dimensions along the shaft that are not proportional.

Figures 6A, 6B:
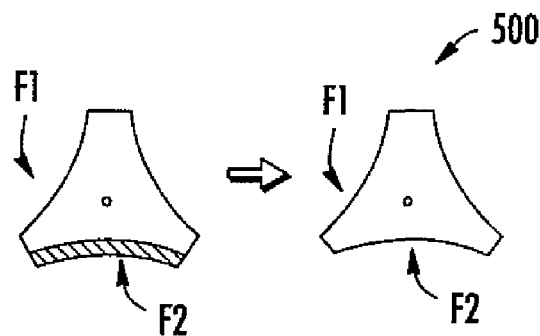
Figures 7A, 7B:
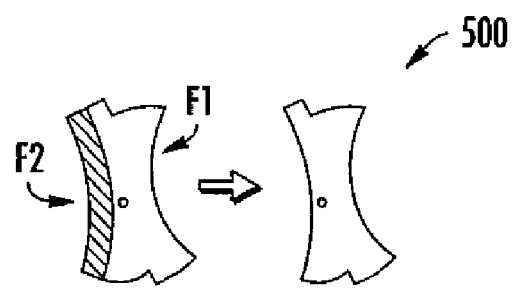
Figures 8A, 8B:
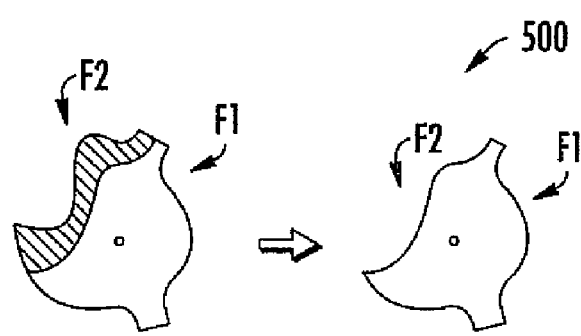

FIGS. 6A-B illustrate an embodiment in which the file 500 includes three flutes. FIG. 6A is a cross-section of the working portion at a first longitudinal point and FIG. 6B is a cross-section of the working portion at a second longitudinal point which is distal to the first longitudinal point. As shown, the second flute F2 has a greater degree of taper with respect to the central axis as compared to the first flute F1. In a similar manner, FIGS. 7A-9B and FIGS. 11A-11B illustrate modified embodiments in which the file has different cross-sectional shapes and/or number of flutes. As shown, in these embodiments, the second flute also has a greater degree of taper with respect to the central axis as compared to the first flute F1. FIGS 10A-10B illustrate an embodiment in which the second flute has greater degree of taper with respect to the central axis as compared to the first flute. However in this embodiment, the dimensions of the second flute also change along the axis of the shaft. In this embodiment, the second flute changes from having a substantially sinusoidal shaped facing surface to a substantially concave shape facing surface. In various embodiments of the invention, the shape of both the facing surfaces of the first and second flutes, or even more flutes, may change along the axis of the shaft. In certain of such embodiments, the shape of the facing surfaces of various flutes may change at different rates along the axis of the shaft than the shape of other facing surfaces. FIG. 12 illustrates an embodiment, in which the flutes are substantially flat and non helical.

The endodontic file 500 with multi-tapered flutes according to the preferred embodiments described above is highly efficacious in cleaning and expanding root canal openings. Multi-tapering of the flutes is particularly advantageous because it provides a technique for controlling (e.g., increasing or reducing) flexibility and/or blade engagement of the file along the axis of the working portion.

The concepts and teachings of the present embodiment are particularly applicable to nickel-titanium alloys and endodontic instruments (files, reamers, obturators, drill bits and the like) fabricated therefrom. However, the invention disclosed herein is not limited specifically to endodontic instruments fabricated from NiTi alloys, but may be practiced with a variety of dental and other medical instruments using any one of a number of other suitable medical-grade alloys. Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An endodontic instrument for cleaning and extirpating a root canal, comprising an elongated shaft having a working portion having a plurality of flutes comprising at least a first flute and a second flute, the flutes having one or more tissue-removing edges, points and/or surfaces defined thereon, the first flute having a first axial taper angle with respect to the longitudinal axis of the working portion and the second flute having a second axial taper angle with respect to the longitudinal axis of the working portion, wherein the first axial taper angle is different than the second axial taper angle along at least a portion of the working portion, and further wherein a first facing surface of the first flute has a cross sectional profile shape and dimension substantially the same as a cross sectional profile shape and dimension of a second facing surface of the second flute at a first longitudinal point of the working portion and wherein the cross sectional profile shape or dimension of the first facing surface is different than the cross sectional profile shape or dimension of the second facing surface at a second longitudinal point of the working portion distal from the first longitudinal point.

2. The endodontic instrument of claim 1, wherein the working portion has a substantially asymmetrical cross sectional shape along at least a portion of its length.

3. The endodontic instrument of claim 1, wherein the first facing surface has a different cross sectional profile shape than the second facing surface along at least a portion of the working portion.

* * * * *